United States Patent [19]
Kulow et al.

[11] Patent Number: 5,172,692
[45] Date of Patent: Dec. 22, 1992

[54] METHOD FOR INFLAMMATORY RESPONSE MANAGEMENT

[76] Inventors: Howard H. Kulow, 880 Bryant Ave., Apt. B, Berea, Ohio 44017; William M. Hunsinger, P.O. Box 6836, Cleveland, Ohio 44101

[21] Appl. No.: 622,769
[22] Filed: Dec. 5, 1990
[51] Int. Cl.$^5$ ............................................. A61N 1/00
[52] U.S. Cl. ............................ 128/24 AA; 128/52; 128/55; 128/57
[58] Field of Search .................. 128/24 R, 24.1, 24.2, 128/24.3, 41, 48, 54–56, 57, 58, 43–45, 421–423

[56] References Cited

U.S. PATENT DOCUMENTS

| | | | |
|---|---|---|---|
| 2,540,792 | 2/1951 | McCready | 128/48 |
| 2,593,982 | 4/1952 | Cash | 128/57 |
| 2,792,830 | 5/1957 | Dacey | 128/24.1 |
| 3,499,437 | 3/1970 | Balamuth | 128/24 |
| 3,862,629 | 1/1975 | Rotta | 128/24 R |
| 4,069,816 | 1/1978 | Yamamura et al. | 128/41 |
| 4,089,989 | 9/1977 | Shaefer | 128/55 |
| 4,102,334 | 7/1978 | Muchisky | 128/55 X |
| 4,312,340 | 1/1982 | Donadelli | 128/421 X |
| 4,538,596 | 9/1985 | Colasante | 128/32 |
| 4,549,535 | 10/1985 | Wing | 128/55 |
| 4,620,543 | 11/1986 | Happenstall et al. | 128/423 R X |
| 4,722,326 | 2/1988 | Ruderian | 128/24.1 |
| 4,845,178 | 7/1989 | Fuxue et al. | 128/419 F |
| 4,850,340 | 7/1989 | Onishi | 128/24.1 |
| 4,895,154 | 1/1990 | Bartell et al. | 128/423 R X |
| 4,919,138 | 4/1990 | Nordenstroöm | 128/421 |

OTHER PUBLICATIONS

Williams, et al., Ed., *Gray's Anatomy, 37th Edition*, Churchill, Livingstone, Edinburgh, 1989.
The Oxford Companion to Medicine, Ultrasonics in Medicine, Oxford University Press, pp. 1404–1406.
The Dornier Add.
Postoperative Nursing, Chapter 24, p. 489.
AMA Encyclopedia of Medicine, p. 588.
Oxford Companion to Medicine, p. 604.
Medical Surgical Nursing, Part Eight, Problems Related to Impaired Protective Mechanisms, pp. 1892–1895.
CIBA clinical Symposia, Wound Healing, vol. 29, No. 3, 1977.

*Primary Examiner*—Gene Mancene
*Assistant Examiner*—L. Thomas
*Attorney, Agent, or Firm*—Fay, Sharpe, Beall, Fagan, Minnich & McKee

[57] ABSTRACT

A therapeutic method for reducing the inflammatory response within an organic structure thereby accelerating the overall healing process. This method comprises the steps of generating a vibrational wave energy flow, determining a treatment area of the organic structure and subjecting the treatment area to the vibrational wave energy flow sufficient to diffuse inflammatory components from the treatment area.

19 Claims, 3 Drawing Sheets

5,172,692

METHOD FOR INFLAMMATORY RESPONSE MANAGEMENT

BACKGROUND OF THE INVENTION

1. Field of the Invention

The present invention relates to the art of wound healing and in particular to management of the inflammatory response subsequent to laceration, elective incision, or impact trauma.

2. Description of Related Art

U.S. Pat. No. 4,048,989 describes a tissue pulsator capable of operating on an area to be treated with a tapping action. When applied to readily palpable tissue, the tapping action produces a pulsating motion in the tissue causing contraction and relaxation of the tissue at frequencies of about 5,000 cycles per minute. A beneficial result is an improved circulation, and a relaxation of tense and contracted tissues. In addition, the function of tissues injured by fractures, surgery, or trauma is restored usually after the healing process is established. Additional uses include low back strain or sprain, tendinitis, rotator cuff lesions, post-fracture edema and stiffness, and psychogenic rheumatism. The tissue pulsator operates in a plane perpendicular to the tissue surface.

A method and apparatus for treatment of organic structures and systems using ultrasonic energy is described in U.S. Pat. No. 3,499,437, wherein coherent wave energy is rapidly anticipated into thermal energy or heat and creates effects mainly due to temperature rise in the underlying hard or soft tissues. Typically, the dosage of energy is necessarily low so as to not damage the treated tissue due to extremes in temperature. Claimed therapeutic applications include increased blood circulation in a given area and more rapid healing of wounds through a so-called micromassage, which micromassage is a periodic compression and extension (or push and pull, pressure and tension) resulting from compressional waves. Other mechanical effects of coherent wave energy include microstreaming or a kind of vibrational pumping causing fluids in organic structures to undergo local circulations which are not ordinarily present. In U.S. Pat. No. 3,499,439, it is believed that the microstreaming effects affect the permeability of cell membranes to promote interchange of substances across those cell membrane boundaries.

Another example of the medical application of energy waves in the form of ultrasound is the kidney stone lithotripter manufactured by Dornier GmbH of the Federal Republic of Germany. In the case of the lithotripter, kidney and gallstones are fragmented without open surgery through the external application of a coherent ultrasound source directed to a point in the patient's body occupied by the kidney or gallstone.

The present invention contemplates a new method which obtains results heretofore not thought possible using the above referred to apparatus and further contemplates a method to provide a simple and safe approach to expediting the overall wound healing process.

SUMMARY OF THE INVENTION

It is an overall advantage of the present invention to provide for a reduction in swelling (edema), redness (erythema), and inflammation (defined pathologically) following laceration, incision, or impact trauma such that the overall rate of healing is increased. This is accomplished through a minimization of the level of inflammatory response to a point where it does not interfere with the healing process itself.

A reduction in pain due to the reduction in swelling and inflammation is also realized due to the reduction of mediators which cause pain. Since swelling near the injury is minimized, there is less stress in the injury locale. Therefore, pain receptors responsive to stretching and compression are not triggered. The fewer receptors which are activated, the less pain resultant from the injury experienced by the patient.

In general, disposal of dead cells is a constant ongoing process. This process does not trigger what is commonly accepted as an inflammatory response. Further, concentrations of inflammatory components including dead cells, below a threshold level, do not trigger an inflammatory response sufficient to delay healing. Concentrations above the threshold level trigger response proportional to the amount in excess of the threshold. Thus generally, the more concentrated the necrotic and other debris, the more severe is the inflammatory response. The present invention works to diffuse and disperse the inflammatory components and substantially reduce the resulting inflammatory response.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof.

DETAILED DESCRIPTION OF THE PREFERRED EMBODIMENT

Figures 1, 2:
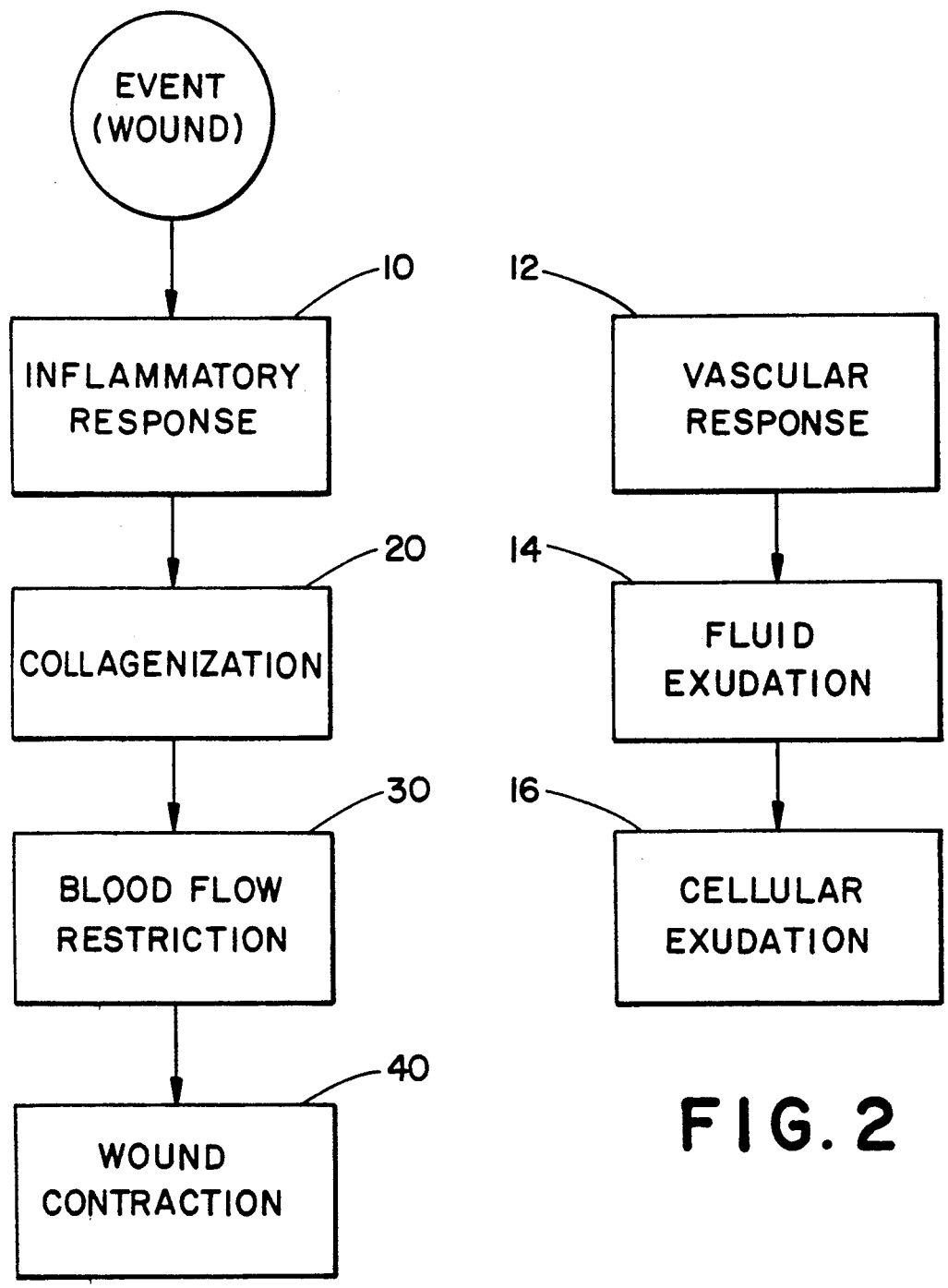
FIG. 1 is a flow chart of a typical wound healing process.
FIG. 2 is a flow chart of a typical inflammatory response process.

Referring to the drawings, wherein the showings are for the purposes of illustrating the preferred embodiment of the invention only and not for the purposes of limiting same, the FIGURES shown a method for accelerating the wound healing process.

Referring first to FIG. 1, a typical wound healing process comprises a number of distinct phases, wherein all wounds, regardless of the type, progress through the phases illustrated, the difference being only in the length of time within each phase for individual wounds.

The first phase, the inflammatory response 10, which commonly lasts for as much as two (2) or more weeks begins immediately following the injury or surgical incision and prepares the tissue so healing itself may take place. Phagocytosis commences wherein leukocytes invade the injured area to ingest bacteria, necrotic tissue and other debris. Fibrinolytic enzyme is secreted by the epithelial cells to permit advancement of these cells across the wound. Capillaries are supported by and follow the fibrin network to reach capillaries on the opposite side of the wound to cannulize, and reinstitute blood flow across the wound. In general then, the first phase of wound healing comprises blood clotting with fibrin deposition, inflammation, phagocytosis of microorganisms and debris, the layering of the epithelial cells over the wound, and the resumption of blood flow across the wound.

In the second phase 20 of the wound healing process, collagen, deposited by fibroblasts, begins replacing the fibrin network. The second phase begins substantially during the first phase (day 3 to 7), overlapping the first phase in part, and extends to approximately fourteen days after the initial tissue damage.

The epithelial tissue generated during the first phase of the wound healing process are regenerated within one week. The underlying, highly vascular new connective tissue is called granulation tissue and is visible through the thin, grayish epithelial layer. The second phase of the wound healing process ends typically when sutures, staples, or metal skin clips are removed.

The third phase 30 of the wound healing process witnesses the build up of collagen to compress the numerous blood vessels restricting blood flow across the wound. This phase ends in the sixth week after surgery or injury.

The final phase 40 of wound healing may last for several months after the tissue damage. Collagen production continues during the final phase as the wound generally shrinks to become scar tissue which is relatively acellular, avascular collagen tissue.

When tissue undergoes injury, whether caused by invasion, cuts, abrasion, collision, heat, cold, chemicals, electricity, compression or stretching of tissue, skin grafts or transplants, or by any other means, the body reacts with specific and nonspecific defense mechanisms to protect the body against invasion of microorganisms and other agents through the site of the wound. The mechanism which accomplishes the above is called the inflammatory response. It is postulated that the use of inflammatory response management as described below will be therapeutic in many other situations including inflammation such as for example arthritis. Regardless of the cause, the inflammatory response serves to protect against infection and to prepare the tissue for healing, and as such always precedes what is commonly viewed as the "healing process".

FIG. 2 illustrates a flow chart of the typical inflammatory response process which comprises the first phase 10 of the healing process shown in FIG. 1. The three major physiologic responses which occur during the inflammatory response are the vascular response 12, fluid exudation 14, and cellular exudation 16. The vascular response 12 (stress response) is a short-lived transitory vaso-constriction followed by short-lived transitory vaso-constriction followed by vaso-dilation. Histamines are substances released at the wound site causing vaso-dilation and increased small-vessel permeability. Mast cells are believed to be the source of histamine along with substances from platelets and leukocytes at the wound site. Kinins are also released at the injury site causing the vaso-dilation. Due to the vaso-dilation, the blood flow in the area is increased (hyperemia), which is observable as redness and heat.

Serous fluid fills the interstitial spaces during the initial twenty-four (24) hours following the injury or invasion, comprising the fluid exudation step 14. As the capillaries begin to become more permeable, increasing colloid osmotic pressure encourages further fluid exudation. Edema is the swelling of the tissue caused by the fluid filling the interstitial spaces.

Cellular exudation 16 occurs as the leukocytes migrate through the capillary walls and into the damaged area immediately adjacent the injured tissue. As chemotactic substances are released from the injured tissues, more and more leukocytes migrate into on the damaged area. Neutrophils, which are polymorphonuclear leukocytes perform a phagocytotic function by ingesting bacteria and dead tissue cells. The neutrophils, having performed their function, die releasing proteolytic enzymes which, in turn, liquify dead neutrophils, bacteria, and other dead cells and collect as pus. This wound exudate, or pus, contains enzymes which facilitate the breakdown of necrotic debris by the monocytes which then transform into macrophages which ingest materials not broken down by the polymorphonuclear leukocytes.

Figure 3:
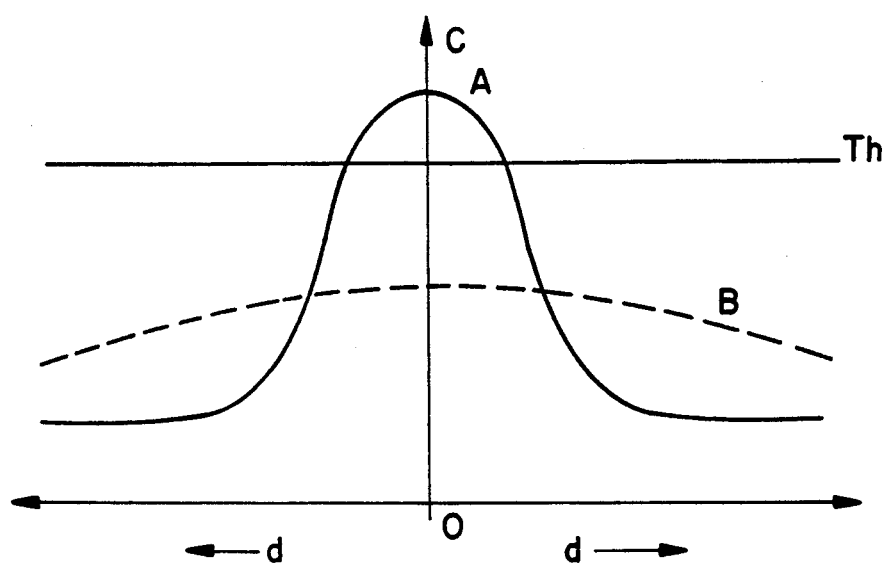
FIG. 3 is a cross sectional view of a surgical wound site illustrating the concentration of inflammatory components and a threshold concentration level.

FIG. 3 shows a profile view of the concentration C of inflammatory components resulting from a typical surgical wound in a direction d transverse to the wound, wherein the wound itself is centered at O in the FIGURE. The breadth and intensity of the inflammatory response is directly related to the quantity of inflammatory components located near the wound site. As shown in the FIGURE, a typical wound site profile A contains a large concentration of inflammatory components at the incision or abrasion itself, whose concentrations decrease exponentially as distance from the wound area is increased in the direction d. A threshold level Th is indicated on the FIGURE to indicate a level of inflammatory components below which the inflammatory response is negligible. In a typical wound profile A, the tissue surrounding the injury contains inflammatory components whose concentrations are sufficiently high to elicit the inflammatory response.

Still referring to FIG. 3, curve B represents the inflammatory component concentration profile in a wound after the method for inflammatory response management described below has been performed. As illustrated in FIG. 3 the peak concentration at the wound site is reduced below a threshold level and is less than that seen for a typical wound A. In other words, the exponential nature of the curve is greatly modified to minimize the amount of tissue targeted by the inflammatory response. Because no "healing" can occur until the inflammation has subsided and pus and dead tissue have been removed, the practice of the method of inflammatory response management described below reduces the time necessary for wound healing by eliminating or greatly reducing the time period required by the inflammatory response itself.

Figure 4:
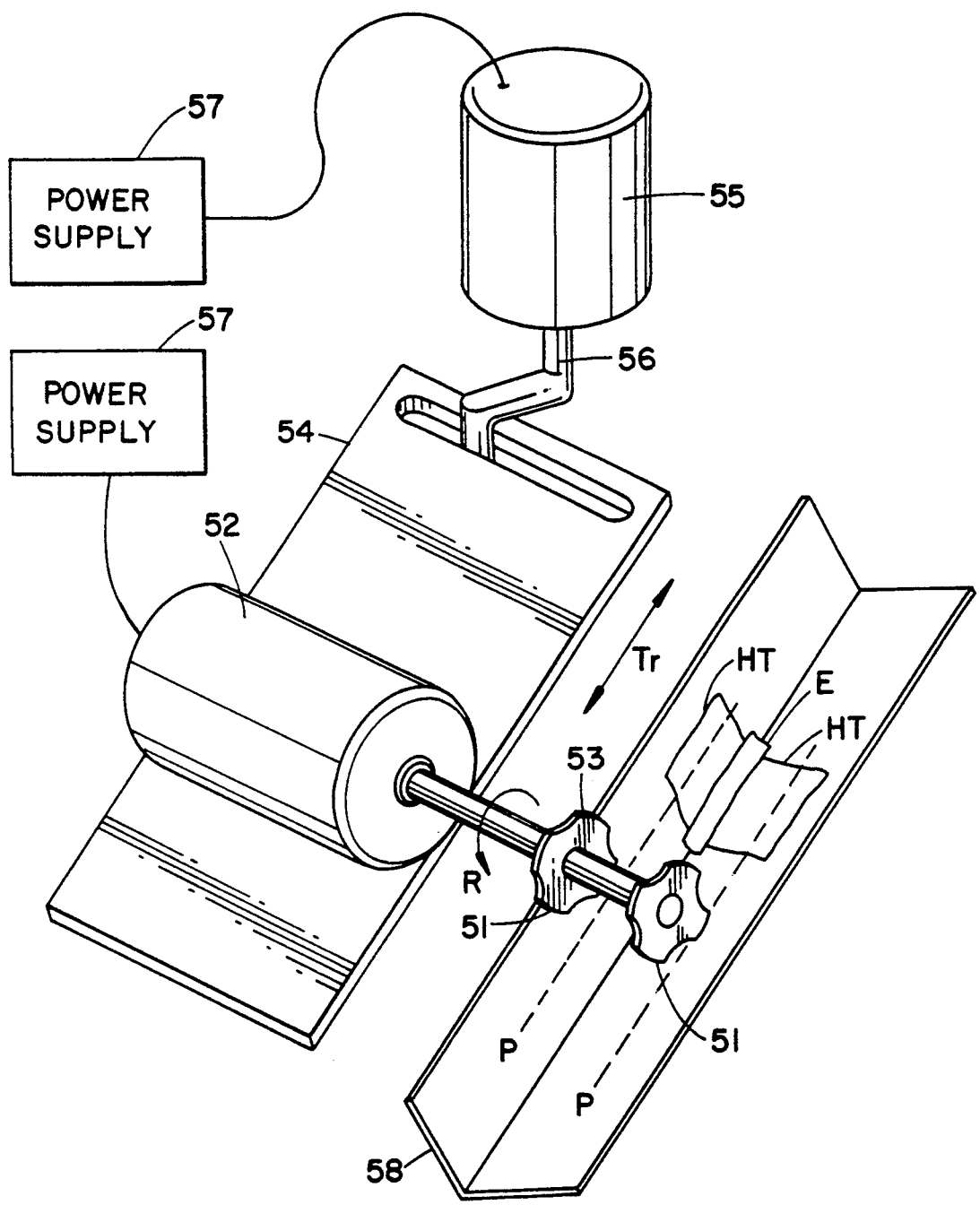
FIG. 4 is a diagrammatical view of an apparatus for wound healing.

Referring now to FIG. 4, a diagrammatical view of an apparatus for practicing a method for inflammatory response management is shown. A pair of small impulse wheels 51 are driven by a first small D.C. motor 52 from three to twenty-two hundred revolutions per minute (300–2200 RPM), the impulse wheels each having four (4) protuberances 53 which can be made to impact tissue adjacent a wound as each wheel rotates. The impulse wheels are separated on the shaft of the D.C. motor 52 by about three quarters (0.750) of an inch. Each of the impulse wheels 51 are about one (1) inch in diameter with the protuberances 53 extending radially about one fourth (0.250) inch. In addition to the rotational dimension R provided by the first motor 52, a reciprocating transverse motion Tr is also imparted to the slidable impulse wheel section 54 by a second D.C.

motor 55 by means of the follower arrangement 56 shown, to "walk" the impulse wheels 51 and the associated tensioning vibrations generated in the target organic tissue thereby, along a straight path P against healthy tissue HT on either side and adjacent a wound E. The apparatus shown increases the rate of wound healing by imparting mechanical energy impulses to the tissue immediately adjacent the wound E to affect the initial responses associated with the healing process.

A pair of variable power supplies 57 provides the necessary energy and control for the D.C. motors 52, 55. Control over the linear traverse rate of the impulse wheel section 54 is directly facilitated by one of the pair of variable power supplies 57 to obtain a range of linear traverse cycle rate (back and forth cycles) in the path P, adjustable for particular applications, such as thirty-six cycles per minute (36 CPM) for example. In the apparatus shown, the path P spans about four (4) inches of linear motion. Control of the rotational speed of the impulse wheels 51 in the rotational dimension R, is similarly facilitated through control over the other variable power supply of the pair 57. The path P is shown as being linear, but may be modified to follow a curvlinear path to better follow the contours of a particular wound/organic structure combination, and may be made to travel distances longer than the four (4) inches shown.

With continued reference to FIG. 4, a stage 58 in the form of a trough is provided to receive an organic structure, such as a laboratory rat for treatment by the pair of impulse wheels 51. The stage 58 is shown as a section of metal angle in alignment with the path P, but may be substituted with any form of apparatus for receiving any organic structure therein.

The energy imparted into the tissue adjacent the wound travels as ripples on a pond through the surrounding tissue including the damaged area itself to increase a permeation and diffusion of the inflammatory components. Along with the dispersion and increased permeation and diffusion, a more rapid drop in the concentration of the effector molecules results, which influences wound healing and inflammation.

The dramatic results are achieved by transferring energy in the form of mechanical pulsations into the tissue surrounding the wound. An improvement over the mechanical apparatus diagrammed in FIG. 4 would be the use of ultrasound wherein the energy envelope is more easily transferrable to the deeper tissues without appreciably affecting the outer surface tissues. That is, being mechanical in character, ultrasonic energy dissipates as it propagates down through the tissues and essentially provides a "through-and-through" kind of effect. However, at frequencies in the range of one to ten million hertz (1-10 MHz), the sound waves can be focused by sound lenses as light waves to particularly select and define a treatment area. Of course, the energy applied to the tissue eventually attenuates to a minimal value as the wave travels through the tissue layers. Power levels of the order of one watt per cubic centimeter (1 W/cm$^2$) of tissue is likely to simulate the motivational force of the apparatus of FIG. 4 and realize equivalent results. An improvement ultrasound provides over the device diagrammed in FIG. 4 is the ability to accurately select a tissue target area for treatment, without affecting otherwise healthy tissue near the wound site and without unnecessary loss of energy in to those healthy tissues.

In either case, application of energy prior to the inflammatory response by way of the rotating pulse wheels diagrammed in FIG. 4 or through ultrasonic, hydraulic, pneumatic, or electro-mechanical techniques, a reduction in the inflammatory response by the diffusion of the concentrations of inflammatory components is achievable. The increase in permeation and diffusion of necrotic and other debris achieves a drop in the concentration of inflammatory components and correspondingly reduces the inflammatory response.

The action of permeation and diffusion may be likened to that involved in the entropic process, wherein energy is applied to non-homogenous material with the resultant tendency toward entropy. Energy applied to a wound site immediately after injury promotes the movement of inflammatory components away from areas of higher concentration to those of lower concentration. By minimizing the local severity of the inflammatory response, early onset of healing is ensured. In addition, the tissue immediately adjacent the injury site is more receptive and better prepared for the ensuing healing process.

Because of the energy imparted to the wound area, tissues on either side of an incision tend to "align" themselves resulting in scars which appear flat, level, and have good alignment along the wound axis. The gross observable effects are minimal redness and swelling, neater and cleaner wounds with little observable exudate. By contrast, scars from untreated wounds show varying degrees of "lumpiness" and misalignment.

Figure 5:
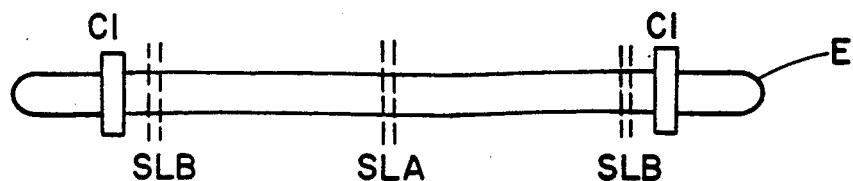
FIG. 5 is a diagrammatical layout of an experimental typical wound site of the method; and, FIG. 6 is a healing versus time curve.

FIG. 5 illustrates the practices followed during an experiment on laboratory rats. A linear incision E was made on the backs of each of the rats, followed by coapting with two surgical clips Cl. Histological samples were taken near the clips Cl at slice SLB, and in the center of the linear incision E at slice SLA.

Experiments were performed on the laboratory rats using the appartus shown in FIG. 4. In the experimental study, three month old female Sprague-Dawley rats weighing 200 grams to 250 grams were used. The rats were anesthetized with ethyl ether inhalation and a toe pinch reflex was used to gauge proper depth of anesthesia. The rats were then shaved on the back and scrubbed with sterile alcohol prep pads before surgery, during which a four centimeter linear incision E was placed through the skin 1.5 centimeters deep on the right side of the rat's lower back midline. The wound was then coapted with two surgical clips Cl.

The anesthetized rats were then placed in the trough 58 of the apparatus diagrammed in FIG. 4, the wound being positioned between the pair of impulse wheels 51 for treatment. The treatment consisted of the use of the first D.C. motor 52 rotating at twenty-two hundred revolutions per minute (2200 RPM) and traversing at a rate of thirty-six cycles per minute (36 CPM) for twenty-five (25) minutes along the path P. To avoid harsh abrasion, a plastic film was placed between the wound and the pair of impulse wheels 51. After treatment, another similar incision was made on the left side of the upper back of each rat. No machine treatment was performed on the second incision. The animals were sacrificed at post operation times of 2, 4, 7, 10, and 14 days, the wounds together with sufficient amount of skin were excised and fixed with 10% formaldehyde. The results of the above described experiments are set forth in the TABLES below.

TABLE I

RESULTS

| SAMPLE | DESCRIPTION |
|---|---|
| 61 | Rat No. 1 - 2 Days - Treated Wound - Slice Location A |
| 62 | Rat No. 2 - 2 Days - Treated Wound - Slice Location A |
| 63 | Rat No. 3 - 2 Days - Treated Wound - Slice Location A |
| 64 | Rat No. 1 - 2 Days - Control Wound - Slice Location A |
| 65 | Rat No. 2 - 2 Days - Control Wound - Slice Location A |
| 66 | Rat No. 3 - 2 Days - Control Wound - Slice Location A |
| 67 | Rat No. 4 - 4 Days - Treated Wound - Slice Location A |
| 68 | Rat No. 4 - 4 Days - Control Wound - Slice Location A |
| 69 | Rat No. 7 - 7 Days - Treated Wound - Slice Location A |
| 70 | Rat No. 8 - 7 Days - Treated Wound - Slice Location A |
| 71 | Rat No. 9 - 7 Days - Treated Wound - Slice Location A |
| 72 | Rat No. 7 - 7 Days - Control Wound - Slice Location A |
| 73 | Rat No. 8 - 7 Days - Control Wound - Slice Location A |
| 74 | Rat No. 9 - 7 Days - Control Wound - Slice Location A |
| 75 | Rat No. 10 - 10 Days - Treated Wound - Slice Location A |
| 76 | Rat No. 11 - 10 Days - Treated Wound - Slice Location A |
| 77 | Rat No. 12 - 10 Days - Treated Wound - Slice Location A |
| 78 | Rat No. 10 - 10 Days - Control Wound - Slice Location A |
| 79 | Rat No. 11 - 10 Days - Control Wound - Slice Location A |
| 80 | Rat No. 12 - 10 Days - Control Wound - Slice Location A |
| 81 | Rat No. 14 - 14 Days - Treated Wound - Slice Location A |
| 82 | Rat No. 14 - 14 Days - Control Wound - Slice Location A |

TABLE II

RESULTS

| SAMPLE | DESCRIPTION |
|---|---|
| 90 | Rat No. 1 - 2 Days - Treated Wound - Slice Location B |
| 91 | Rat No. 2 - 2 Days - Treated Wound - Slice Location B |
| 92 | Rat No. 3 - 2 Days - Treated Wound - Slice Location B |
| 93 | Rat No. 1 - 2 Days - Control Wound - Slice Location B |
| 94 | Rat No. 2 - 2 Days - Control Wound - Slice Location B |
| 95 | Rat No. 3 - 2 Days - Control Wound - Slice Location B |
| 96 | Rat No. 4 - 4 Days - Treated Wound - Slice Location B |
| 97 | Rat No. 4 - 4 Days - Control Wound - Slice Location B |
| 98 | Rat No. 7 - 7 Days - Treated Wound - Slice Location B |
| 99 | Rat No. 8 - 7 Days - Treated Wound - Slice Location B |
| 100 | Rat No. 9 - 7 Days - Treated Wound - Slice Location B |
| 101 | Rat No. 7 - 7 Days - Control Wound - Slice Location B |
| 102 | Rat No. 8 - 7 Days - Control Wound - Slice Location B |
| 103 | Rat No. 9 - 7 Days - Control Wound - Slice Location B |
| 104 | Rat No. 10 - 10 Days - Treated Wound - Slice Location B |
| 105 | Rat No. 11 - 10 Days - Treated Wound - Slice Location B |
| 106 | Rat No. 12 - 10 Days - Treated Wound - Slice Location B |
| 107 | Rat No. 10 - 10 Days - Control Wound - Slice Location B |
| 108 | Rat No. 11 - 10 Days - Control Wound - Slice Location B |
| 109 | Rat No. 12 - 10 Days - Control Wound - Slice Location B |
| 110 | Rat No. 14 - 14 Days - Treated Wound - Slice Location B |
| 111 | Rat No. 14 - 14 Days - Control Wound - Slice Location B |

TABLE III

HISTOLOGICAL EVALUATION

| TIME AFTER TREATMENT | SAMPLE | SCAB FORMATION | INCISION "INTENTION" | INFLAMMATION | EDEMA | FIBROSIS | EPIDERMAL OVERGROWTH |
|---|---|---|---|---|---|---|---|
| 2 DAYS | 61 | 2 | 1 | 2 | 2 | 3 | 1 |
|  | 62 | 2 | 2 | 2 | 3 | 3 | 1 |
|  | 63 | 2 | 2 | 2 | 2 | 3 | 1 |
|  | 64 | 4 | 4 | 4 | 4 | 4 | 0 |
|  | 65 | 3 | 4 | 4 | 4 | 3 | 0 |
|  | 66 | 3 | 3 | 4 | 4 | 4 | 1 |
| 4 DAYS | 67 | — | — | 2 | 2 | 3 | — |
|  | 68 | 4 | 4 | 4 | 4 | 3 | 0 |
| 7 DAYS | 69 | 2 | 2 | 2 | 1 | 2 | 4 |
|  | 70 | 2 | 2 | 1 | 0 | 1 | 4 |
|  | 71 | 1 | 1 | 1 | 0 | 1 | 4 |
|  | 72 | 2 | 2 | 2 | 1 | 3 | 4 |
|  | 73 | 1 | 2 | 3 | 2 | 3 | 4 |
|  | 74 | 3 | 3 | 3 | 3 | 3 | 1 |
| 10 DAYS | 75 | 1 | 2 | 2 | 0 | 2 | 4 |
|  | 76 | 0 | 2 | 1 | 0 | 1 | 4 |
|  | 77 | 0 | 1 | 1 | 0 | 1 | 4 |
|  | 78 | 1 | 2 | 1 | 1 | 2 | 4 |
|  | 79 | 1 | 1 | 1 | 1 | 2 | 4 |
|  | 80 | 1 | 2 | 2 | 1 | 2 | 4 |
| 14 DAYS | 81 | 0 | 1 | 1 | 0 | 1 | 4 |
|  | 82 | 1 | 2 | 1 | 1 | 2 | 4 |

TABLE IV

HISTOLOGICAL EVALUATION

| TIME AFTER TREATMENT | SAMPLE | SCAB FORMATION | INCISION "INTENTION" | INFLAMMATION | EDEMA | FIBROSIS | EPIDERMAL OVERGROWTH |
|---|---|---|---|---|---|---|---|
| 2 DAYS | 90 | 2 | 3 | 2 | 2 | 3 | 0 |
|  | 91 | 2 | 1 | 1 | 1 | 3 | 1 |
|  | 92 | 2 | 1 | 1 | 1 | 3 | 1 |
|  | 93 | 3 | 2 | 2 | 3 | 4 | 0 |
|  | 94 | 3 | 3 | 2 | 2 | 4 | 0 |
|  | 95 | 4 | 4 | 3 | 3 | 4 | 0 |
| 4 DAYS | 96 | 2 | 2 | 2 | 1 | 3 | 3 |
|  | 97 | 4 | 4 | 4 | 3 | 0 | 1 |
| 7 DAYS | 98 | 1 | 0 | 1 | 0 | 2 | 4 |
|  | 99 | 1 | 0 | 0 | 0 | 2 | 4 |

TABLE IV-continued

| TIME AFTER TREATMENT | SAMPLE | SCAB FORMATION | HISTOLOGICAL EVALUATION | | | | EPIDERMAL OVERGROWTH |
|---|---|---|---|---|---|---|---|
| | | | INCISION "INTENTION" | INFLAMMATION | EDEMA | FIBROSIS | |
| | 100 | 0 | 0 | 0 | 0 | 2 | 4 |
| | 101 | 2 | 2 | 2 | 2 | 3 | 4 |
| | 102 | 1 | 2 | 2 | 2 | 3 | 4 |
| | 103 | 1 | 2 | 1 | 1 | 3 | 4 |
| 10 DAYS | 104 | 1 | 1 | 0 | 0 | 1 | 4 |
| | 105 | 0 | 1 | 0 | 0 | 1 | 4 |
| | 106 | 0 | 1 | 0 | 0 | 1 | 4 |
| | 107 | 1 | 1 | 0 | 0 | 2 | 4 |
| | 108 | 0 | 0 | 0 | 0 | 3 | 4 |
| | 109 | 0 | 1 | 0 | 0 | 3 | 4 |
| 14 DAYS | 110 | 0 | 0 | 0 | 0 | 0 | 4 |
| | 111 | 0 | 2 | 0 | 0 | 1 | 4 |

TABLE V

SCALE OF HISTOLOGICAL REACTION

| ASSIGNED SCORE | SCAB FORMATION | INCISION "INTENTION" | INFLAMMATION | EDEMA | FIBROSIS* | EPIDERMAL OVERGROWTH |
|---|---|---|---|---|---|---|
| 0 | None | Zero | None | None | Severe | None |
| 1 | Minimal | Minimal | Minimal | Minimal | Marked | 25% |
| 2 | Moderate | Moderate | Moderate | Moderate | Moderate | 50% |
| 3 | Marked | Marked | Marked | Marked | Minimal | 75% |
| 4 | Severe | Severe (Wide) | Severe | Severe | None | Complete |

DEFINITIONS for TABLES III-V

Scab Formation - a measure of the extent of scab formation.

Incision "Intention" - a measure of the width of the incision. This is related to wound healing by first or second intention. It is related to the distance or space between the two sides of the incision.

Inflammation - a measure of the degree of inflammatory response present in the incision site.

Edema - a measure of the edema or extracellular fluid present within the incision site.

Fibrosis - a measure of the fibrosis in the wound healing of the incision site. Note that the fibrosis scale gives a zero assigned score for severe or extensive fibrosis versus an assigned score of four for no fibrosis.

Epidermal Overgrowth - a measure of the overgrowth of the epidermis across the incision site. This occurs even though the dermis has not completely healed.

Sample 62 is a representation of a wound two (2) days following treatment using the above-described process. As indicated in the Tables, scab formation on the skin surface is minimal to moderate and the approximation of the two sides of the incision, incision intention, is minimal. This is an indication that the width of the incision following the treatment is minimal and the two sides of the wound have approximated excellently. Inflammation is minimal to none, no acute and/or chronic inflammation is identified in any of the levels of skin, edema is minimal to none, and fibrosis is minimal.

Sample 65 in the Tables above indicates the incision site of an untreated rat two (2) days after the incision. Scab formation is marked and is obvious by a thick scab on the skin surface. The two sides of the incision have not approximated and the incision intention is marked, indicating that the width of the incision is markedly wide. Moderate acute inflammation is seen in the subdermal areas. Marked inflammation is also seen below the muscle layer. Moderate to minimal edema is seen within the wound site. However, no fibrosis is seen in the wound site. Comparison between samples 62 and 65 indicates that the untreated incision has a much slower healing response.

Sample 71 in the Tables above indicates another incision site, but at seven (7) days following the treatment discussed above. Minimal scab formation is present on the skin surface and the width of the incision is minimal, that is, the incision intention is minimal. Minimal acute and chronic inflammation are seen within the incision site and no edema is present. Marked fibrosis and scar formation has occurred within the incision site. Complete epidermal overgrowth on the surface of the skin has occurred. It is clear that the incision site seven (7) days after treatment indicates progression of the wound into the final stages of wound healing.

Sample 74 in the Tables above indicates an incision site of another rat seven (7) days after the incision, but without treatment. Scab formation is marked and a thick scab is present on the skin surface. The sides of the incision are still widely separated indicating marked incision intention. Within the wound site between the two sides of the incision, marked acute inflammation, marked edema, and minimal fibrosis are present. Comparison between samples 71 and 74 indicates that the treatment has increased the healing response, by decreasing inflammation, decreasing incision intention or width of the injury, decreasing edema, and increasing fibrosis.

Figure 6:
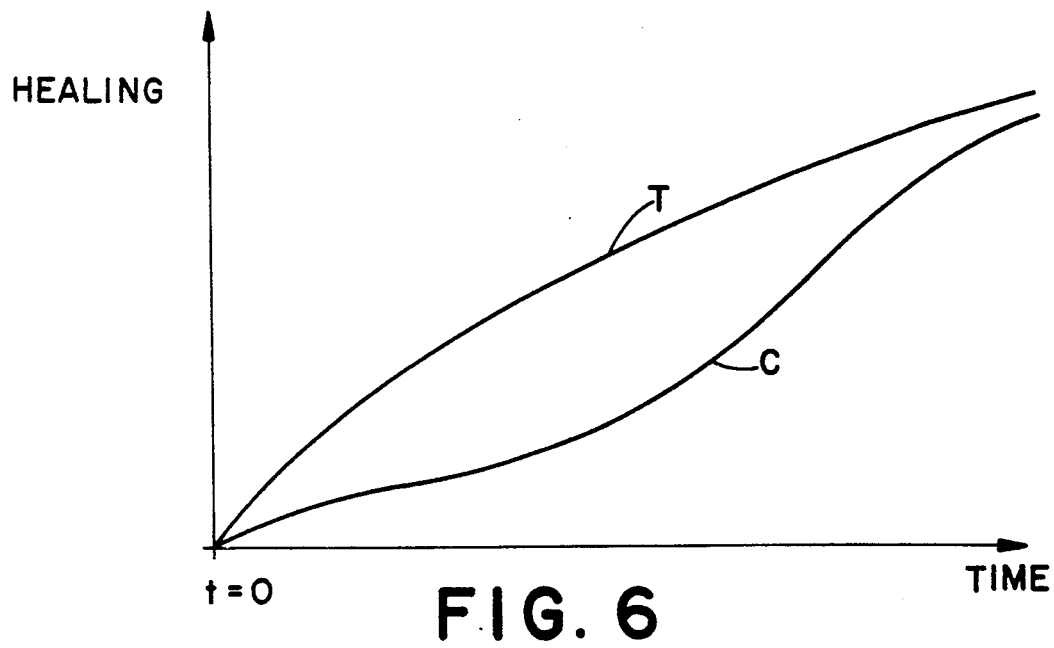

Referring now to FIG. 6, a simple healing versus time curve is illustrated. As seen in the curve, the ordinant axis forms a healing scale and the abscissa is a time scale. In general terms, the healing process begins at time $t=0$, immediately following injury or incision. A typical healing response without the application of the above-described method follows the curve labeled C. However, using the method of the present invention, a healing process approximating the curve labeled T is obtainable resulting in an overall increase in wound healing.

The invention has been described with reference to the preferred embodiment. Obviously, modifications and alterations will occur to others upon a reading and understanding of this specification. In addition, the treatment of laboratory rats and results are easily extrapolated to treatment of humans using techniques well known in the art of medicine. It is our intention to include all such modifications and alterations insofar as they come within the scope of the appended claims or the equivalents thereof.

Having thus described an embodiment of the invention, we claim:

1. In an organic structure having tissue exhibiting a healing process comprising a plurality of sequential phases including an initial inflammatory response, a method of controlling said inflammatory response to minimize interference with regeneration and repair of said tissue in said organic structure subsequent to wound sustainment, the method comprising the steps of:
generating a vibrational wave energy flow by means of a vibrational wave energy source;
determining a treatment area of an organic structure expected to exhibit the inflammatory response; and,
subjecting the treatment area to the vibrational wave energy flow substantially immediately after said wound sustainment and during said inflammatory response for a predetermined period of time sufficient to diffuse inflammatory components, having accumulated in the treatment area, into the non-treatment area of the organic structure.

2. The method of claim 1 further comprising placing the organic structure immediately adjacent the vibrational wave energy source.

3. The method of claim 2 further comprising placing the organic structure immediately adjacent as to contact the vibrational wave energy source.

4. The method of claim 1 wherein the generating step comprises generating a coherent acoustic wave energy flow.

5. The method of claim 1 wherein the generating step comprises generating a coherent ultrasonic wave energy flow.

6. The method of claim 1 wherein the subjecting step further comprises subjecting the treatment area to the vibrational wave energy flow for a predetermined period of time sufficient to diffuse the inflammatory components to a concentration below a predetermined first threshold level below which the inflammatory response is determined to be negligible.

7. The method of claim 1 wherein the generating step comprises generating a mechanical wave energy flow by means of a mechanical wave energy source.

8. A method for diffusing and dispersing inflammatory components from a wound site area of an organic structure into a non-wound site area of the organic structure, the method comprising the steps of:
generating a wave energy flow by means of an energy source;
determining a treatment area of the organic structure expected to exhibit an inflammatory response; and,
subjecting the treatment area to the wave energy flow substantially immediately after wound sustainment to diffuse said inflammatory components having accumulated in the treatment area into the non-treatment area of the organic structure.

9. A method for maintaining alignment of tissue adjacent either side of a laceration of an organic structure substantially immediately after sustaining laceration comprising:
generating a vibrational wave energy flow by means of a vibrational wave energy source;
determining a treatment area of an organic structure expected to exhibit an inflammatory response; and,
subjecting the treatment area to the vibrational wave energy flow for a predetermined period of time during said inflammatory response and substantially immediately after said laceration sufficient to diffuse inflammatory components, that accumulate and cause a swelling in the treatment area, into the non-treatment area of the organic structure and sufficient to align tissue of the organic structure immediately adjacent the laceration.

10. The method of claim 1 wherein the subjecting step further comprises subjecting the treatment area to the vibrational wave energy flow during said inflammatory response and before said inflammatory components accumulate in the treatment area to a predetermined concentration level below which the inflammatory response is determined to be negligible.

11. The method of claim 1 wherein the subjecting step further comprises subjecting the treatment area to the vibrational wave energy flow substantially immediately after said wound sustainment and before said inflammatory response.

12. A method according to claim 8 wherein the subjecting step includes subjecting the treatment area to said mechanical wave energy flow substantially immediately after said wound sustainment and during said inflammatory response sufficient to diffuse said inflammatory components having accumulated in the treatment area into the non-treatment area of the organic structure.

13. A method according to claim 8 wherein the subjecting step includes subjecting the treatment area to said mechanical wave energy flow substantially immediately after said wound sustainment and during said inflammatory response sufficient to diffuse said inflammatory components having accumulated in the treatment area into the non-treatment area of the organic structure until the concentration of inflammatory components in the treatment area is below a predetermined threshold level.

14. A method according to claim 8 wherein the subjecting step includes subjecting the treatment area to a vibrational wave energy flow substantially immediately after said wound sustainment.

15. A method according to claim 14 wherein the subjecting step includes subjecting the treatment area to said vibrational wave energy flow substantially immediately after said wound sustainment and during said inflammatory response sufficient to diffuse said inflammatory components having accumulated in the treatment area into the non-treatment area of the organic structure.

16. A method according to claim 14 wherein the subjecting step includes subjecting the treatment area to said vibrational wave energy flow substantially immediately after said wound sustainment and during said inflammatory response sufficient to diffuse said inflammatory components having accumulated in the treatment area into the non-treatment area of the organic structure until the concentration of inflammatory components in the treatment area is below a predetermined threshold level.

17. A method according to claim 8 wherein the subjecting step includes subjecting the treatment area to a vibrational mechanical wave energy flow substantially immediately after said wound sustainment.

18. A method according to claim 17 wherein the subjecting step includes subjecting the treatment area to said vibrational mechanical wave energy flow substantially immediately after said wound sustainment and during said inflammatory response sufficient to diffuse said inflammatory components having accumulated in the treatment area into the non-treatment area of the organic structure.

19. A method according to claim 17 wherein the subjecting step includes subjecting the treatment area to said vibrational mechanical wave energy flow substantially immediately after said wound sustainment and throughout said inflammatory response sufficient to diffuse said inflammatory components having accumulated in the treatment area into the non-treatment area of the organic structure until the concentration of inflammatory components in the treatment area is below a predetermined threshold level.

* * * * *